(12) United States Patent
Grant et al.

(10) Patent No.: US 7,418,355 B2
(45) Date of Patent: Aug. 26, 2008

(54) METHOD AND SYSTEM FOR MONITORING A PISTON ROD

(75) Inventors: John W. Grant, Gardnerville, NV (US); Olga Malakhova, Minden, NV (US); Roger Hala, Gardnerville, NV (US); Brian F. Howard, Issaquah, WA (US)

(73) Assignee: General Electric Company, Schenectady, NY (US)

( * ) Notice: Subject to any disclaimer, the term of this patent is extended or adjusted under 35 U.S.C. 154(b) by 487 days.

(21) Appl. No.: 11/324,710

(22) Filed: Jan. 3, 2006

(65) Prior Publication Data

US 2007/0151342 A1    Jul. 5, 2007

(51) Int. Cl.
*G01F 17/00* (2006.01)
(52) U.S. Cl. ........................................... 702/56
(58) Field of Classification Search .................... 702/56
See application file for complete search history.

(56) References Cited

U.S. PATENT DOCUMENTS

| | | | |
|---|---|---|---|
| 5,507,253 A * | 4/1996 | Lowi, Jr. ..................... 123/56.9 |
| 5,610,339 A * | 3/1997 | Haseley et al. ................. 73/660 |
| 6,292,757 B1 * | 9/2001 | Flanagan et al. ............ 702/138 |
| 6,997,101 B2 | 2/2006 | Lyu |
| 7,007,563 B2 | 3/2006 | Spiegl et al. |
| 7,056,097 B2 | 6/2006 | Lake |
| 7,186,094 B2 | 3/2007 | Edlund et al. |

\* cited by examiner

*Primary Examiner*—John E. Barlow, Jr.
*Assistant Examiner*—Aditya S Bhat
(74) *Attorney, Agent, or Firm*—Armstrong Teasdale LLP

(57) ABSTRACT

A method for monitoring a condition of a piston rod of a reciprocating compressor is provided. The piston rod having a length defined between a piston end and a crosshead end. The method includes positioning a first probe with respect to the piston rod along a x-axis and positioning a second probe with respect to the piston rod along a y-axis coplanar with and substantially perpendicular to the x-axis. A current ringing vibration amplitude greater than ten times a maximum of a one-hour average and a noise floor at a ringing frequency is detected, and a bent rod condition is diagnosed.

20 Claims, 3 Drawing Sheets

METHOD AND SYSTEM FOR MONITORING A PISTON ROD

BACKGROUND OF THE INVENTION

This invention relates generally to monitoring the operation of machinery and, more particularly, to a method and system for monitoring a condition of a machine component.

In many high pressure machinery applications, such as reciprocating compressor applications, long piston rods experience bent rod anomaly. Relatively large alternating forces act on a piston rod during compressor operation. Further, when liquid is injected into the compressor cylinder, the piston head and/or the piston rod is subjected to acute impacts. With each liquid impact, the generally straight piston rod becomes unstable and, as a result of repeated impact, may be permanently bent. The bent shape of the piston rod will affect the compressor efficiency. Further, when compared to a straight piston rod, a bent piston rod is subjected to elevated stresses resulting from periodically varying forces. Thus, fatigue deterioration of the bent piston rod is more pertinent. The personnel who operate the reciprocating compressors need to be notified of bent piston rod problems before severe machine damage occurs.

BRIEF DESCRIPTION OF THE INVENTION

In one aspect, the present invention provides a method for monitoring a condition of a piston rod of a reciprocating compressor. The piston rod has a length defined between a piston end and a crosshead end. The method includes positioning a first probe with respect to the piston rod along a x-axis and positioning a second probe with respect to the piston rod along a y-axis coplanar with and substantially perpendicular to the x-axis. A current ringing vibration amplitude greater than ten times a maximum of a one-hour average and a noise floor at a ringing frequency is detected, and a bent rod condition is diagnosed.

In another aspect, the present invention provides a method for monitoring a condition of a piston rod of a reciprocating compressor. The method includes positioning a first probe positioned with respect to the piston rod along a x-axis and positioning a second probe with respect to the piston rod along a y-axis coplanar with and substantially perpendicular to the x-axis. A compressor operation mode is checked. An indication is generated if the machine speed has been within design limitations for at least two minutes. A ringing vibration state is determined. Each of the first probe and the second probe is analyzed to determine whether the first probe and/or the second probe detects a current ringing vibration amplitude greater than ten times a maximum one-hour average and a noise floor at a ringing frequency. A 6-second buffer gap average is compared against a one-hour buffer average for each probe independently. An indication that a possible bent rod condition exists is generated if a difference between the 6-second buffer average and the one-hour buffer average for at least one probe is greater than a defined value for 6 consequent rule processing cycles.

In another aspect, the present invention provides a computer program for monitoring a piston rod condition. The computer program is configured to detect a current ringing vibration amplitude greater than ten times a maximum of a one-hour average and a noise floor at a ringing frequency utilizing at least one of a first probe positioned with respect to the piston rod along a x-axis and a second probe positioned with respect to the piston rod along a y-axis coplanar with and substantially perpendicular to the x-axis, and diagnose a bent rod condition.

DETAILED DESCRIPTION OF THE INVENTION

The present invention provides a method and system for monitoring a condition of at least one compressor component, such as a piston rod. Although the present invention is described below in reference to its application in connection with and operation of a reciprocating compressor, it is obvious to those skilled in the art and guided by the teachings herein provided that the invention is likewise applicable to any suitable machine and/or machine component having any suitable number of pistons, chambers and/or valves, for example.

Figure 1:
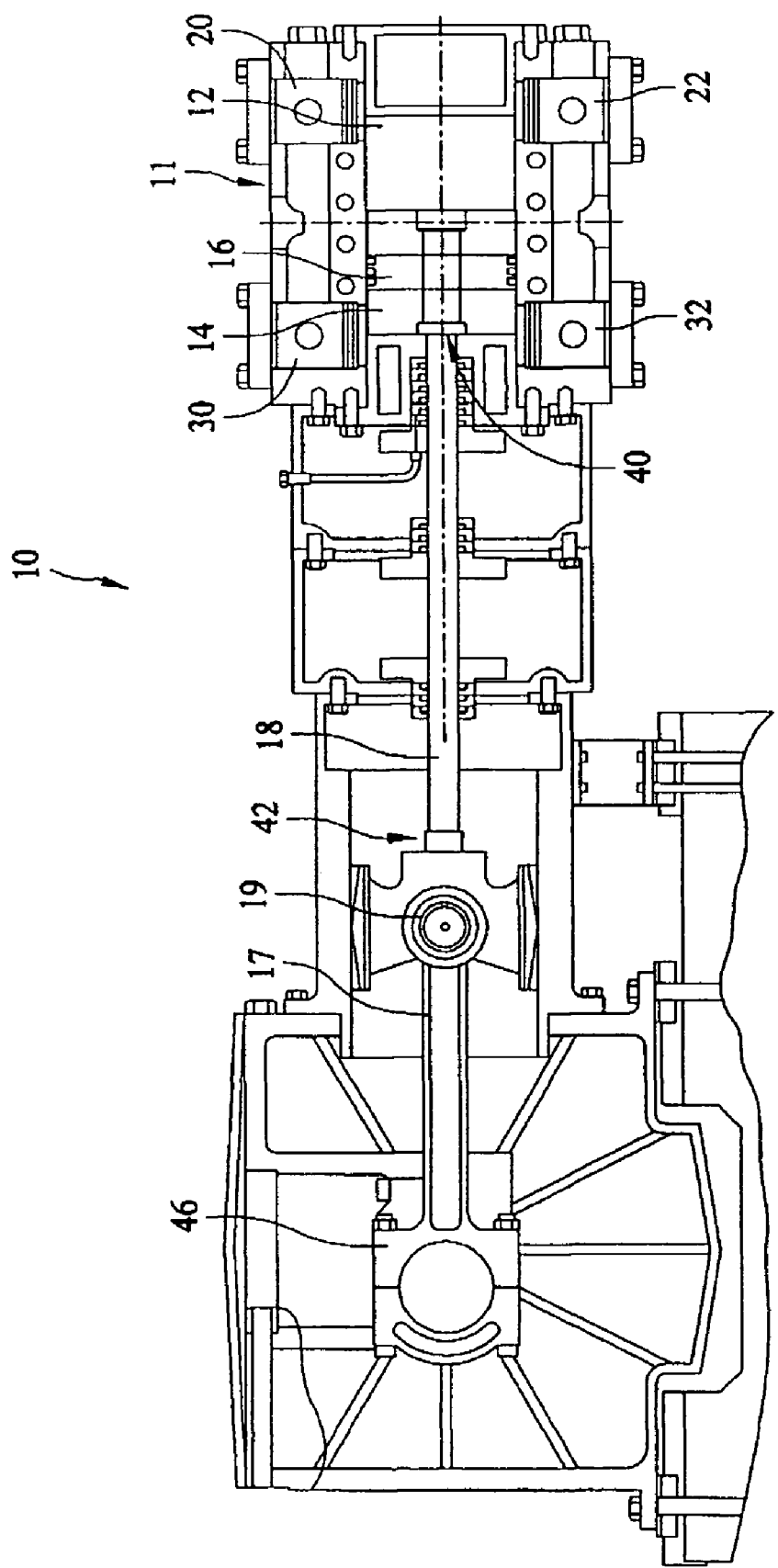
FIG. 1 is a partial schematic view of an exemplary reciprocating compressor.

In one embodiment, a reciprocating compressor 10 includes a cylinder 11 defining a first or head end (HE) chamber 12 and an opposing second or crank end (CE) chamber 14, as shown in FIG. 1. A piston head 16 is positioned within cylinder 11 and movable within cylinder 11 in a reciprocating motion. A piston rod 18 operatively couples the linear motion of piston head 16 to a rotating shaft of compressor 10 through crosshead pin 19 and connecting rod 17. A HE suction valve 20 is operatively coupled with respect to HE chamber 12. Suction valve 20 opens to allow a gas or gas mixture to enter HE chamber 12 as piston head 16 moves outwardly with respect to HE chamber 12 during a suction stroke to draw the gas or gas mixture into HE chamber 12. A HE discharge valve 22 is also operatively coupled with respect to HE chamber 12. Discharge valve 22 opens to allow a compressed gas or gas mixture to exit HE chamber 12 as piston head 16 moves inwardly with respect to HE chamber 12 during a compression stroke to force or direct the compressed gas or gas mixture out of HE chamber 12. Similarly, a CE suction valve 30 is operatively coupled with respect to CE chamber 14. Suction valve 30 opens to allow the gas or gas mixture to enter CE chamber 14 as piston head 16 moves outwardly with respect to CE chamber 14 to draw the gas or gas mixture into CE chamber 14. A CE discharge valve 32 is also operatively coupled with respect to CE chamber 14. Discharge valve 32 opens to allow a compressed gas or gas mixture to exit CE chamber 14 as piston head 16 moves inwardly with respect to CE chamber 14 to force or direct the compressed gas or gas mixture out of CE chamber 14.

Figure 2:
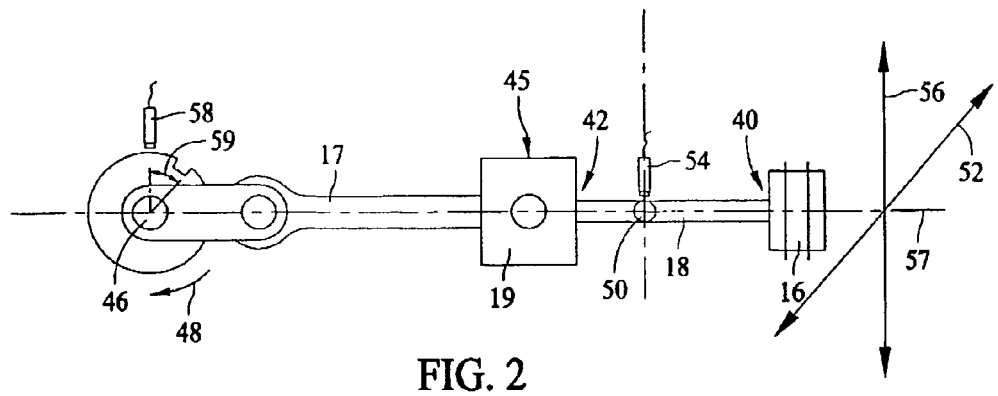
FIG. 2 is a schematic view of an exemplary piston for a reciprocating compressor.

Referring further to FIG. 2, in one embodiment, a piston rod length is defined as a length between piston head 16 and connecting rod 44. In this embodiment, piston rod 18 has a length to diameter ratio of about 20:1 to about 30:1. Piston rods having a smaller length to diameter ratio typically do not bend during compressor operation. Piston rod 18 includes a first end 40 coupled to piston head 16 and an opposing second end 42 coupled to connecting rod 17 through crosshead 19. Connecting rod 17 is coupled to a crankshaft 46 that rotates in a clockwise direction, as shown by reference arrow 48 in FIG. 2. A first or radial proximity probe 50 is positioned with respect to piston rod 18 to sense displacement of piston rod 18 in a first or generally horizontal radial direction along a x-axis 52, perpendicular to a y-axis 56 and a z-axis 57. A second proximity probe 54 is positioned with respect to piston rod 18 to sense displacement of piston rod 18 in a second or vertical direction along y-axis 56, coplanar with and perpendicular to x-axis 52. A third proximity probe 58 is positioned with respect to crankshaft 46 to sense rotational or angular displacement 59 of crankshaft 46. Third probe 58 is configured as a timing marker to mark an angular position of crankshaft 46 and derived linear extension of piston rod 18 during a suction stroke and/or a compression stroke.

In this embodiment, first end 40 of piston rod 18 is assumed to be coupled to piston head 16 in a fixed condition and second end 42 is assumed to be coupled in a pivotally movable condition with respect to crosshead location 45. Under these assumptions, a bent mode for piston rod 18, e.g., wherein piston rod 18 is bent, can be described by the following equation:

$$f(x) = f_{max} \frac{z_o}{2\pi} \left( \frac{x}{L_{rod}} - \frac{\sin\left(z_o \frac{x}{L_{rod}}\right)}{\sin(z_o)} \right) \quad \text{(Eq. 1)}$$

where f(x) is a piston rod deflection at a distance from a center of the crosshead, $L_{rod}$ is a piston rod length, $f_{max}$ is a maximum deflection of the piston rod and $z_0$=4.49341 is the root of equation tg(z)=z. The bent mode according to Eq. (1) becomes stable after a loss of stability of a straight-line rod shape.

Over a full piston stroke, beginning at top dead center (TDC), the crankshaft angular position, ϑ, is changing from 0 degrees to 360 degrees. The distance from the center of crosshead 45 to a position of a plane within which probes 50 and 52 are fixed will vary in accordance with the following equation:

$$x(\vartheta) = L + r - L\sqrt{1 - \left(\frac{r}{L}\right)^2 \sin^2\vartheta} + r\cos\vartheta + x_{probe} \quad \text{(Eq. 2)}$$

where $x_{probe}$ is a distance from the center of crosshead 45 to probe 50 when piston head 16 is at the TDC, r is a crankshaft radius and L is a connecting rod length.

Figure 3:
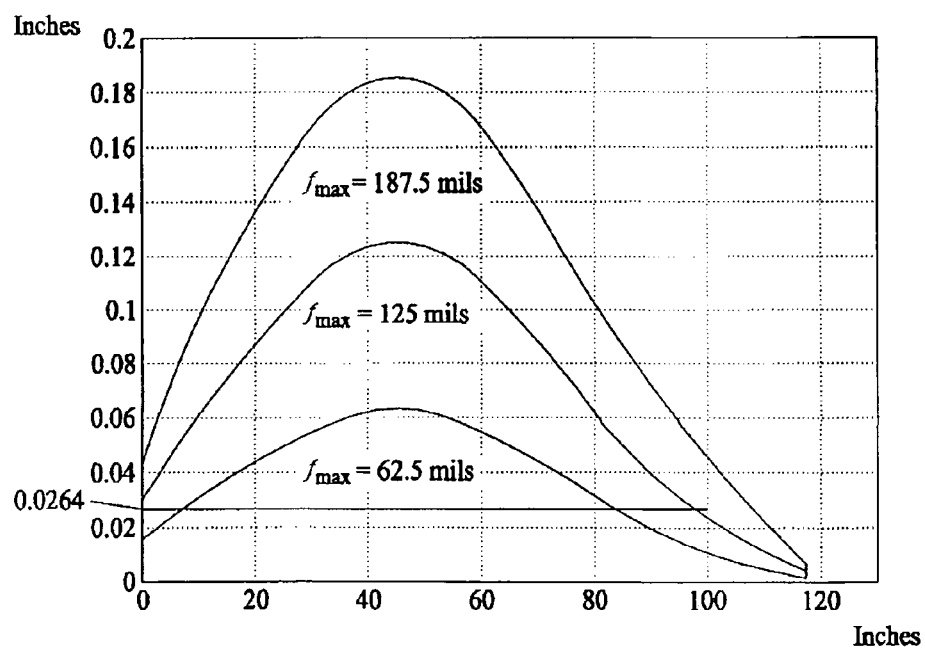
FIG. 3 is a graphical representation of average gap voltage step change versus probe position for bent rods.

A prediction of piston rod deflection observed by probe 50 during one rotation of crankshaft 46 is determined by substituting Eq. (2) into Eq. (1). Further, characteristics of the signal, such as peak-to-peak displacement, average gap and/or 1× and 2× variables, can be estimated. Depending upon the machine parameters and probe position, the characteristics demonstrate different behavior. Analysis is performed to select an average gap voltage to consistently indicate a rod bending condition. FIG. 3 illustrates a plot of average gap voltage verses probe position. The plot facilitates adjusting a gap step change set point for the bent rod anomaly. Referring to FIG. 3, the set point depends on a position of probe 50 and an expected maximum deflection value. For example, if a distance from crosshead 45 to probe 50 is 100 inches and a maximum deflection value for a bent rod is 125 mils, then probe 50 is expected to observe a gap step change of 26.4 mils.

In one embodiment, a method and system for monitoring a compressor piston rod is provided. The system is configured to detect 100 a bent rod condition. In a particular embodiment, the method and system utilize a first proximity probe 50 fixed along x-axis 52 and second proximity probe 54 fixed along y-axis 56 coplanar with and substantially perpendicular to x-axis 52. Further, the system is configured to monitor a static suction pressure measurement, a discharge pressure measurement and a machine speed input for detect a potential bent rod anomaly.

Figure 4:
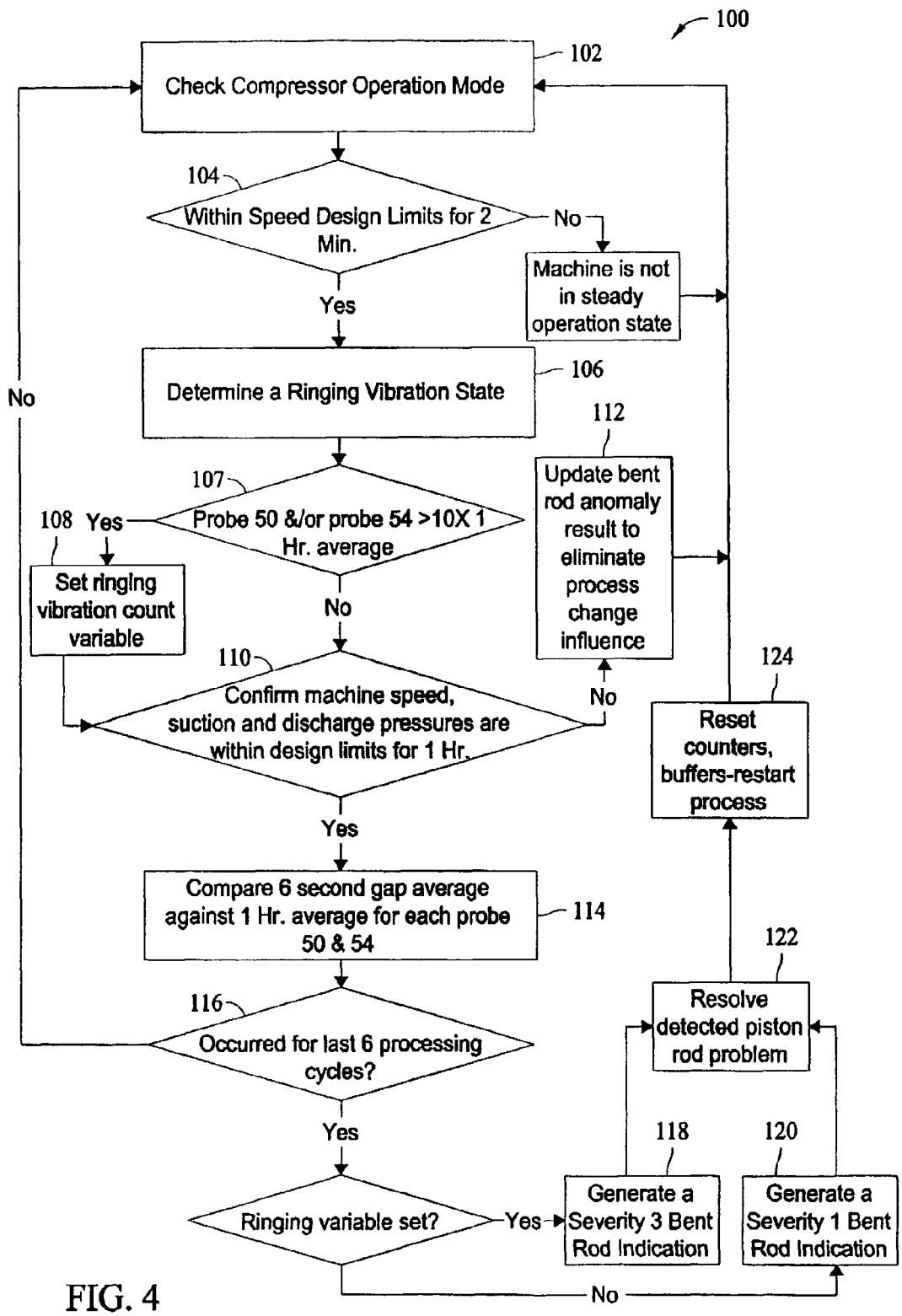
FIG. 4 is a block diagram of a method for monitoring a condition of a piston rod.

Referring to FIG. 4, the method initially includes checking whether a Compressor Operation Mode is true 102. In one embodiment, checking 102 includes a rule set that determines whether a machine speed during a last two minutes of machine operation is within a machine speed variation range between a minimum speed and a maximum speed. If, within a two minute buffer, the machine speed is within the machine speed variation range, a YES indication is generated 104 and transmitted to the system. The Compressor Operation Mode will be true if the machine speed has been within design limitations for at least two minutes. A Ringing Vibration State is then determined 106 using a rule set. Data generated through and/or collected from first probe 50 and second probe 54 are analyzed 107 to determine whether first probe 50 and/or second probe 54 detects or senses a current ringing vibration amplitude greater than ten times a maximum one-hour average and/or a noise floor at a ringing frequency. If the previous ringing vibration amplitude did not meet the above condition for any of two channels, the average value is updated then a ringing vibration count variable is set 108.

In one embodiment, the Ringing Vibration State is determined to ensure that each of a machine speed, a suction pressure and a discharge pressure has been within a design variation limit for one hour. A confirmation that the machine speed, the suction pressure and the discharge pressure are within the design variation limits for one hour 110 indicates that the machine is working properly. Thus, the possibility of a process change influence, rather than a bent piston rod 18, is eliminated and a bent rod anomaly result is updated 112. Alternatively, if confirmation is made that the machine is working properly, for each probe 50 and 54 independently, a 6-second buffer gap average is compared against a one-hour buffer average 114. If a difference between the 6-second buffer average and the one-hour buffer average for at least one probe 50 and 54 is greater than a selected or defined value for 6 consequent rule processing cycles, an indication is generated that a possible bent rod condition exists 116. The possible bent rod condition 116 is reported for each current 6-second buffer gap that is within +/−10% of a detected step-changed gap. In one embodiment, if a possible bent rod condition is detected for at least one probe 50 and 54 and a Ringing Vibration Count is greater than zero, a severity 3 BENT ROD indication is generated 118. Conversely, if the possible bent rod condition is detected for at least one probe 50 and 54 and the Ringing Vibration Count is equal to zero, a severity 1 BENT ROD indication is generated 120. After the detected piston rod problem, such as a bent piston rod, has been resolved 122, for example, by replacing the bent piston rod, the Ringing Vibration Count is set to zero automatically or manually when machine restart is detected 124. As a result of machine restart, the buffers used for calculating average values are reset.

In one embodiment, a computer program is configured for monitoring a piston rod condition utilizing probes 50, 54, 58. The computer program is embodied on a computer readable medium for monitoring a condition of piston rod 18, and includes a code segment configured to detect a current ringing vibration amplitude. If the detected current ringing vibration amplitude is greater than ten times a maximum of a one-hour average and a noise floor at a ringing frequency, a possible bent rod condition is diagnosed.

In one embodiment, the computer program is configured to confirm that each of a machine speed, a suction pressure and a discharge pressure is within a design variation limit for an hour. If this confirmation is made, a possibility of a process change influence is eliminated and a bent gap anomaly result is updated. Conversely, if the machine is not working properly, no confirmation will be made. The computer program is configured to compare a 6-second buffer gap average against a one-hour buffer average for each probe 50 and 54 independently. A possible bent rod condition indication is generated if a difference between the 6-second buffer gap average and the one-hour buffer average for at least one probe 50 and 54 is greater than a defined value for 6 consequent rule processing cycles. The possible bent rod condition indication will be generated for each current 6-second buffer average gap step that is within +/−10% of a detected step-change gap. A SEVERITY 3 BENT ROD indication is generated if a possible bent rod condition is detected for at least one probe 50 and 54 and a Ringing Vibration Count is greater than zero. A SEVERITY 1 BENT ROD indication is generated if the possible bent rod condition is detected for at least one probe 50 and 54 and a Ringing Vibration Count is equal to zero.

The above-described method and system for monitoring a piston rod allows a condition of reciprocating compressor piston rods to be monitored in a cost-effective and reliable manner. More specifically, the method and system facilitates detection of an actual or potential bent piston rod condition during reciprocating compressor operation. As a result, a condition of a reciprocating compressor piston rod can be reliably and efficiently monitored.

Exemplary embodiments of a method and system for monitoring a condition of a reciprocating compressor piston rod are described above in detail. The method and system are not limited to the specific embodiments described herein, but rather, steps of the method and/or components of the system may be utilized independently and separately from other steps and/or components described herein. Further, the described method steps and/or system components can also be defined in, or used in combination with, other methods and/or systems, and are not limited to practice with only the method and system as described herein.

While the invention has been described in terms of various specific embodiments, those skilled in the art will recognize that the invention can be practiced with modification within the spirit and scope of the claims.

What is claimed is:

1. A method for monitoring a condition of a piston rod of a reciprocating compressor, said piston rod having a length defined between a piston end and a crosshead end, said method comprising:
    positioning a first probe with respect to the piston rod along a x-axis and positioning a second probe with respect to the piston rod along a y-axis coplanar with and substantially perpendicular to the x-axis;
    detecting a current ringing vibration amplitude greater than ten times a maximum of a one-hour average and a noise floor at a ringing frequency; and
    diagnosing a bent rod condition.

2. A method in accordance with claim 1 further comprising verifying that a machine speed is within a design limit for at least two minutes.

3. A method in accordance with claim 2 further comprising determining whether at least one of a current ringing vibration amplitude is greater than 10 times a maximum of a one-hour average and a noise floor at a ringing frequency, and a previous ringing vibration amplitude is greater than 10 times a maximum of a one-hour average and a noise floor at a ringing frequency.

4. A method in accordance with claim 3 further comprising increasing a ringing vibration count variable by one, if at least one of the current ringing vibration amplitude is greater than 10 times a maximum of a one-hour average and a noise floor at a ringing frequency, and the previous ringing vibration amplitude is greater than 10 times a maximum of a one-hour average and a noise floor at a ringing frequency.

5. A method in accordance with claim 1 further comprising:
    confirming that each of a machine speed, a suction pressure and a discharge pressure is within a design variation limit for an hour;
    eliminating a possibility of a process change influence; and
    updating a bent rod anomaly result.

6. A method in accordance with claim 1 further comprising comparing a 6-second buffer gap average against a one-hour buffer average for each of the first probe and the second probe.

7. A method in accordance with claim 6 further comprising generating a possible bent rod condition indication if a difference between the 6-second buffer gap average and the one-hour buffer average for at least one of the first probe and the second probe is greater than a defined value for 6 consequent rule processing cycles.

8. A method in accordance with claim 7 further comprising generating the possible bent rod condition indication if a current 6-second buffer average gap step is within +/−10% of a detected step-change gap.

9. A method in accordance with claim 7 further comprising generating a SEVERITY 3 BENT ROD indication if a possible bent rod condition is detected for at least one probe and a ringing vibration count is greater than zero.

10. A method in accordance with claim 7 further comprising generating a SEVERITY 1 BENT ROD indication if the possible bent rod condition is detected for at least one probe and a ringing vibration count is equal to zero.

11. A method for monitoring a condition of a piston rod of a reciprocating compressor, said piston rod having a length defined between a piston end and a crosshead end, said method comprising:
    positioning a first probe with respect to the piston rod along a x-axis and positioning a second probe with respect to the piston rod along a y-axis coplanar with and substantially perpendicular to the x-axis;
    checking a compressor operation mode;
    generating an indication if the machine speed has been within design limitations for at least two minutes;
    determine a ringing vibration state;
    analyzing each of the first probe and the second probe to determine whether at least one of first probe and the second probe detects a current ringing vibration amplitude greater than ten times a maximum one-hour average and a noise floor at a ringing frequency;
    comparing a 6-second buffer gap average against a one-hour buffer average for each probe independently; and
    generating an indication that a possible bent rod condition exists if a difference between the 6-second buffer average and the one-hour buffer average for at least one probe is greater than a defined value for 6 consequent rule processing cycles.

12. A method in accordance with claim 11 further comprising generating a SEVERITY 3 BENT ROD indication if a possible bent rod condition is detected for at least one probe and a ringing vibration count is greater than zero.

13. A method in accordance with claim 11 further comprising generating a SEVERITY 1 BENT ROD indication if the possible bent rod condition is detected for at least one probe and the ringing vibration count is equal to zero.

14. A method in accordance with claim 11 further comprising resolving the detected piston rod problem.

15. A method in accordance with claim 14 further comprising:
   restarting the machine;
   resetting the ringing vibration count to zero; and
   setting the buffers used for calculating average values.

16. A method in accordance with claim 11 increasing a ringing vibration count variable by one if the previous ringing vibration amplitude did not meet the above condition for any of two channels.

17. A method in accordance with claim 11 further comprising:
   confirming that the machine speed, the suction pressure and the discharge pressure are within the design variation limits for one hour indicates that the machine is working properly;
   eliminating the possibility of a process change influence; and
   updating a bent rod anomaly result.

18. A computer program embodied on a computer readable medium for monitoring a condition of a piston rod positioned with respect to at least one of a first chamber and a second chamber of a reciprocating compressor, said computer program comprising a code segment configured to:
   detect a current ringing vibration amplitude greater than ten times a maximum of a one-hour average and a noise floor at a ringing frequency utilizing at least one of a first probe positioned with respect to the piston rod along a x-axis and a second probe positioned with respect to the piston rod along a y-axis coplanar with and substantially perpendicular to the x-axis; and
   diagnosing a bent rod condition.

19. A computer program in accordance with claim 18 further configured to:
   confirm that each of a machine speed, a suction pressure and a discharge pressure is within a design variation limit for an hour;
   eliminate a possibility of a process change influence; and
   update a bent rod anomaly result.

20. A computer program in accordance with claim 18 further configured to:
   compare a 6-second buffer gap average against a one-hour buffer average for each of a first probe positioned with respect to the piston rod along a x-axis and a second probe with respect to the piston rod along a y-axis coplanar with and substantially perpendicular to the x-axis;
   generate a possible bent rod condition indication if a difference between the 6-second buffer gap average and the one-hour buffer average for at least one of the first probe and the second probe is greater than a defined value for 6 consequent rule processing cycles;
   generate the possible bent rod condition indication if a current 6-second buffer average gap step is within +/−10% of a detected step-change gap;
   generate a SEVERITY 3 BENT ROD indication if a possible bent rod condition is detected for at least one probe and a ringing vibration count is greater than zero; and
   generate a SEVERITY 1 BENT ROD indication if the possible bent rod condition is detected for at least one probe and a ringing vibration count is equal to zero.

* * * * *